United States Patent [19]

Kern et al.

[11] Patent Number: 4,551,529
[45] Date of Patent: Nov. 5, 1985

[54] GUANINE-$N^7$-OXIDE

[75] Inventors: Donald L. Kern, Dearborn; Gerard C. Hokanson; James C. French, both of Ann Arbor, all of Mich.

[73] Assignee: Warner-Lambert Company, Morris Plains, N.J.

[21] Appl. No.: 539,517

[22] Filed: Oct. 6, 1983

[51] Int. Cl.$^4$ .................. C07D 473/18; A61K 31/52; C12P 17/18; C12R 1/04
[52] U.S. Cl. .................................. 544/265; 435/119; 435/826
[58] Field of Search ................. 544/264, 265; 424/253

[56] References Cited

U.S. PATENT DOCUMENTS 3,920,664  11/1975  Clemens et al. ................. 260/285.5
4,166,182   8/1979  Kornfeld et al. ................... 424/261

OTHER PUBLICATIONS

Brown G. et al. *Cancer Research* 25:986–991 (1965).
Delia & Brown, G., *J. Org. Chem.* 31:178–181, (1966).
Sugiura & Brown, G., *Cancer Research* 27:925–931 (1967).
Wölke & Brown, G., *J. Org. Chem.* 34:978–981 (1969).
Wölke et al., *J. Org. Chem.*, 34:981–983, (1969).
Watson et al., *J. Org. Chem.* 38:3046–3048, (1973).
Watson, *J. Org. Chem.* 39:2911–2916, (1974).
Brown, R. et al., *J. Chem. Soc., Perkin Trans. 1* 9:pp. 1003–1009, (1977).
*Chemical Abstracts* 87:84942r, 89:210598n, 70:115132g.
*Organic Syntheses*, collective vol. 3, pp. 262–267, John Wiley & Sons, New York, 1955.
Livingston et al., *J. Am. Chem. Soc.*, vol 47, pp. 2069–2082, (1925).

*Primary Examiner*—Donald G. Daus
*Assistant Examiner*—Stephen M. Kapner
*Attorney, Agent, or Firm*—Jerry F. Janssen

[57] ABSTRACT

A purified isolate of an actinomycete identified as ATCC 39364 is capable of producing the antimicrobial-/antitumor compound 2-amino-1,9-dihydro-6H-purine-6-one-7-oxide, commonly known as guanine-$N^7$-oxide.

Guanine-$N^7$-oxide is produced by cultivating isolate ATCC 39364 under aerobic conditions in a culture medium containing assimilable sources of carbon and nitrogen until a substantial amount of the compound is produced and thereafter isolating the compound.

The antibiotic/antitumor compound guanine-$N^7$-oxide and pharmaceutical compositions comprising this compound or one of its pharmaceutically acceptable salts together with a pharmaceutically acceptable carrier are also disclosed as is a method of treating microbial infections in a mammal or of treating tumors in a mammal.

5 Claims, No Drawings

GUANINE-N[7]-OXIDE

BACKGROUND OF THE INVENTION

Certain guanine-N-oxides, particularly the N[1]-, N[3]-, and N[9]-oxides have been known in the literature for some time. G. B. Brown and his co-workers have conducted a series of studies on guanine-N-oxides.

In 1965, Brown, et al. [*Cancer Research,* 25:986-991 (1965)] reported the oxidation of guanine with hydrogen peroxide in trifluoroacetic acid to produce an unidentified N-oxide having oncogenic properties.

In a later paper, Delia and Brown (*J. Org. Chem.,* 31:178-181 (1966)] reported their conclusions that the unidentified guanine-N-oxide was the N[7]-oxide, compound Ia.

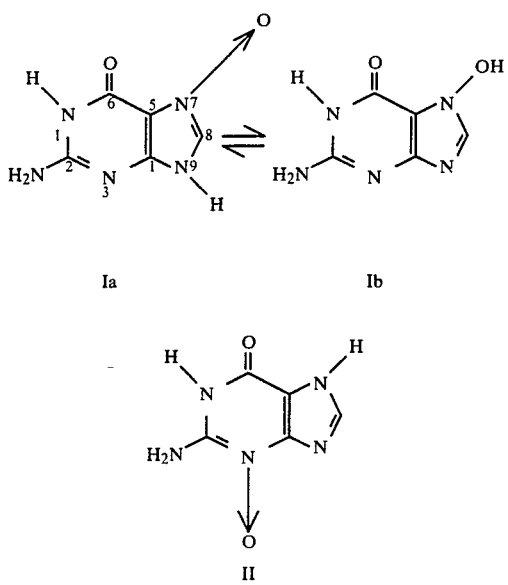

Ia  Ib

II

Subsequently, Brown suggested [*Cancer Research,* 27:925-931 (1967)] that the material which they had produced which exhibited oncogenic properties was the 7-hydroxyguanine tautomer, Ib. However, Wölcke and Brown [*J. Org. Chem.,* 34:978-981 (1969)] showed that the guanine N-oxide which they had reported and discussed in the earlier papers was not guanine-N[7]-oxide, but was instead guanine-N[3]-oxide, compound II. The incorrect structure had been assigned to the material which they had produced on the basis of the infrared spectrum of a known degradation product.

In addition to the above-described synthesis of guanine-N[3]-oxide, the synthesis of guanine-N[1]-oxide [Brown, et al., *J. Org. Chem.,* 38:3046-3048 (1973)] and guanine-N[9]-oxide [Watson, *J. Org. Chem.,* 39:2911-2916 (1974)] have also reported.

SUMMARY OF THE INVENTION

To the best of the knowledge of the inventors, 2-amino-1,9-dihydro-6H-purin-6-one-7-oxide, also commonly designated guanine-N[7]-oxide, is not previously known. It has been found however, in accordance with the present invention, that guanine-N[7]-oxide is produced by aerobic fermentation using an unidentified isolate of actinomycete, herein designated ATCC 39364. Moreover, in accordance with the present invention, the compound has been found to possess antimicrobial and antitumor properties.

Thus, in accordance with one aspect of this invention, there is provided 2-amino-1,9-dihydro-6H-purin-6-one-7-oxide, and the pharmaceutically acceptable salts thereof.

In accordance with a second aspect of this invention, there are provided pharmaceutical compositions for treating microbial infections or for treating tumors in a mammal, the compositions including an effective amount of 2-amino-1,9-dihydro-6H-purin-6-one-7-oxide or one or more pharmaceutically acceptable salts thereof in combination with a suitable pharmaceutically acceptable carrier.

In accordance with a third aspect of the present invention, there is provided a method of treating microbial infections or of treating tumors in a mammal comprising administering to a mammal in need of such treatment an effective amount of 2-amino-1,9-dihydro-6H-purin-6-one-7-oxide.

In accordance with a fourth aspect of the present invention, there is provided a pure isolate of an actinomycete having the identifying characteristics of ATCC 39364 which isolate is capable of producing 2-amino-1,9-dihydro-6H-purin-6-one-7-oxide under conditions of aerobic fermentation.

In accordance with a fifth aspect of the present invention, there is provided a method of producing 2-amino-1,9-dihydro-6H-purin-6-one-7-oxide, comprising the cultivation of a pure isolate of actinomycete ATCC 39364 under aerobic fermentative conditions in a culture medium including assimilable sources of carbon and nitrogen until a sufficient quantity of 2-amino-1,9-dihydro-6H-purin-6-one-7-oxide is produced, and thereafter isolating said 2-amino-1,9-dihydro-6H-purin-6-one-7-oxide.

DETAILED DESCRIPTION

Throughout this specification the common name guanine-N[7]-oxide will be used in place of the formal IUPAC name for the compound 2-amino-1,9-dihydro-6H-purin-6-one-7-oxide.

The compound, guanine-N[7]-oxide, is capable of existing in several tautomeric forms. The present invention contemplates all possible tautomeric forms of the compound, such as Ia–If, and other possible tautomers not shown.

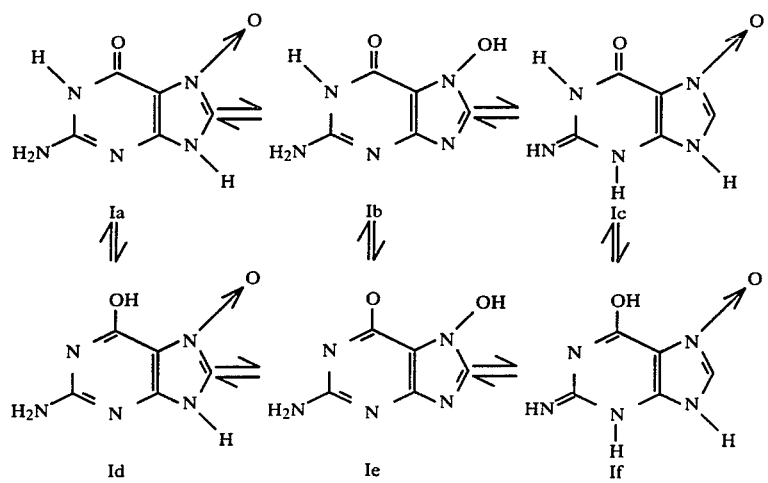

The actinomycete organism of the present invention which is capable of producing guanine-$N^7$-oxide was obtained from a soil sample collected in North Carolina, USA. The organism was isolated from the soil sample by standard plating techniques using a suitable agar medium containing inorganic salts such as potassium dihydrogen phosphate, magnesium sulfate, and ferrous sulfate, and carbon substrates such as glycerol and asparagine. The organism was plated onto the agar medium and incubated under a favorable temperature, particularly 45° C., to allow for development of the organism.

The guanine-$N^7$-oxide producing organism that was isolated from the soil sample by the agar plating technique is an as yet unidentified isolate of actinomycete and has been deposited with the American Type Culture Collection, Rockville, Md. 20852, where it is being maintained in their permanent culture collection as ATCC 39364. This organism is also being maintained as a dormant culture in lyophile tubes, cryogenic vials, and in soil tubes in the Warner-Lambert/Parke-Davis Culture Collection, 2800 Plymouth Road, Ann Arbor, Mich. 48105, where it bears the designation WP-875.

The compound guanine-$N^7$-oxide, which exhibits both antimicrobial and antitumor properties, is produced by actinomycete isolate ATCC 39364 during aerobic fermentation under controlled conditions. The fermentation medium consists of sources of carbon, nitrogen, minerals, and growth factors. Examples of suitable carbon sources are glycerol and various simple sugars such as glucose, mannose, fructose, xylose, ribose, or other carbohydrate and carbohydrate-containing substances such as dextrin, starch, corn meal and whey. The normal quantity of carbon source material in the culture medium generally varies between about 0.1 to 10 percent by weight.

Suitable nitrogen sources for the culture medium include inorganic or mixed inorganic/organic nitrogenous compounds. Examples of such materials are cottonseed meal, soybean meal, corn germ flour, corn steep liquor, distillers solubles, peanut meal peptonized milk, and various ammonium salts.

The addition of minerals and growth factors are also helpful in the fermentative production of guanine-$N^7$-oxide by isolate ATCC 39364. Examples of suitable minerals for the culture medium are potassium dihydrogen phosphate, sodium chloride, ferrous sulfate, calcium carbonate, cobalt chloride, and zinc sulfate. Growth factors are provided by such sources as various yeast and milk by-products.

The preferred method of producing guanine-$N^7$-oxide in accordance with the present invention is by submerged culture fermentation of isolate ATCC 39364. According to this embodiment of the invention, the fermentation medium ingredients are prepared in suspension and the resulting suspension is adjusted to a pH value preferably between about pH 4 to about pH 8. The culture medium is then sterilized by autoclaving or steam heating, cooled to a suitable temperature between 16° C.–45° C., and then inoculated with the microorganism. Fermentation is carried out with aeration and agitation, until sufficient quantities of guanine-$N^7$-oxide are produced, usually within two to ten days under these conditions.

In the submerged culture method, fermentation is carried out in shake-flasks or in stationary tank fermentors. In shake-flasks, aeration is effected by agitation of the flask, causing efficient mixing of the culture medium with air. In stationary tank fermentors, agitation is provided by impellers in the form of disc turbines, vaned discs, open turbines or marine propellers. Aeration is provided by sparging air or oxygen into the fermentation mixture during agitation.

The examples which follow illustrate methods by which the antimicrobial/antitumor compound guanine-$N^7$-oxide is obtained. The examples are not to be read as limiting the scope of the invention as it is defined by the appended claims, but are merely illustrative of the present invention.

Fermentative Production of Guanine-$N^7$-oxide

Shake-Flask Fermentation

EXAMPLE 1

Isolate ATCC 39364 in its dormant state was transferred to an agar slant tube containing sterile CIM 23 culture medium and incubated for 7 to 14 days at 28° C. A portion of the resulting microbial growth was used to inoculate an 18×150 mm tube containing 5 ml of SD-05 seed medium. The seed tube culture was shaken at 33° C. on a rotary gyratory shaker at 170 rpm for three to four days.

TABLE I

| CIM 23 Culture Medium | |
|---|---|
| Amidex corn starch | 10 g |
| N—Z amine, Type A | 2 g |
| Beef Extract (Difco) | 1 g |
| Yeast Extract (Difco) | 1 g |
| Cobalt chloride pentahydrate | 20 mg |
| Agar | 20 g |
| Distilled water | 1000 ml |

TABLE II

| SD-05 Culture Medium | |
|---|---|
| Amberex 1003 (Amber Labs) | 5 g |
| Glucose monohydrate (Cerelose) | 1 g |
| Dextrin-Amidex B411 (Corn Products) | 24 g |
| N—Z-Case (Humko Sheffield) | 5 g |
| Spray dried meat solubles (Daylin Labs) | 3 g |
| Calcium carbonate | 2 g |
| Distilled water | 1000 ml |

EXAMPLE 2

A 1.0 ml portion of the microbial growth from the seed tube of Example 1 was transferred to a 300-ml shake-flask containing 50 ml of SM-30 screening medium. The inoculated shake-flask was incubated at 24° C. for four days with shaking on a rotary gyratory shaker at 170 rpm (5 cm throw). The production of guanine-$N^7$-oxide by isolate ATCC 39364 was first observed during this shake-flask fermentation step.

To confirm the production of guanine-$N^7$-oxide by isolate ATCC 39364, another microbial seed was prepared, and 2 ml of this was used to inoculate a second 50-ml sample of SM-30 screening medium contained in a 300-ml shake-flask. This shake-flask was incubated at 33° C. with shaking (170 rpm, 5 cm throw) for four days. The fermentation beer from the above examples after four days of fermentation appeared creamy in color with good mycelial growth. The pH of the culture medium at the end of the four day period was in the range of pH 5.5 to pH 6.0.

TABLE III

| SM-30 Screening Medium | |
|---|---|
| Cerelose | 15 g |
| Dextrin | 10 g |
| Pharmamedia | 6.5 g |
| Fish meal | 3.5 g |
| Torula yeast | 2.5 g |
| Distilled water | 1000 ml |

The production of guanine-$N^7$-oxide by isolate ATCC 39364 in the above-described shake-flask experiments was observed by screening the fermentation beer against the microorganism *Streptococcus faecalis* 05045. This organism was seeded on agar plates containing AM-9 assay medium in one case, and AM-10 assay medium in another. Paper discs 12.7 mm in diameter were impregnated with the fermentation beer and laid on the seeded agar plate and incubated overnight at 37° C. The diameter of the zones of inhibition of bacterial growth around the paper discs indicated the presence of the antimicrobial compound, and the size of the growth inhibition zone correlated with the different amounts of the antimicrobial compound in the fermentation beer in each shake-flask sample.

TABLE IV

| AM-9 Assay Medium | |
|---|---|
| Potassium monohydrogen phosphate | 3.9 g |
| Dextrose | 25.0 g |
| Sodium citrate dihydrate | 34.4 g |
| Casein hydrolysate | 6.2 g |
| L-Asparagine | 375 mg |
| L-Tryptophan | 125 mg |
| L-Cysteine | 312.5 mg |
| Glutathione | 3.1 mg |
| Thiamine hydrochloride | 250 μg |
| Riboflavin | 625 μg |
| Calcium pantothenate | 500 μg |
| Nicotinic acid | 500 μg |
| p-Aminobenzoic acid | 625 μg |
| Biotin | 12.5 μg |
| Pyridoxine hydrochloride | 2.5 μg |
| Folic acid | 500 μg |
| Sodium chloride | 12.5 μg |
| Magnesium sulfate | 250 μg |
| Ferrous sulfate | 12.5 μg |
| Manganese sulfate monohydrate | 125 μg |
| Tween 80 | 62.5 μg |
| Agar | 15 g |
| Distilled water | 1000 ml |

TABLE V

| AM-10 Assay Medium | |
|---|---|
| Potassium monohydrogen phosphate | 3.9 g |
| Dextrose | 25.0 g |
| Sodium citrate dihydrate | 34.4 g |
| Casein hydrolysate | 6.2 g |
| L-Asparagine | 375 mg |
| L-Tryptophan | 125 mg |
| L-Cysteine | 312.5 mg |
| Glutathione | 3.1 mg |
| Thiamine hydrochloride | 250 μg |
| Riboflavin | 625 μg |
| Calcium pantothenate | 500 μg |
| Nicotinic acid | 500 μg |
| p-Aminobenzoic acid | 625 μg |
| Biotin | 12.5 μg |
| Pyridoxine hydrochloride | 2.5 μg |
| Folic acid | 500 μg |
| Sodium chloride | 12.5 μg |
| Magnesium sulfate | 250 μg |
| Ferrous sulfate | 12.5 μg |
| Manganese sulfate monohydrate | 125 μg |
| Tween 80 | 62.5 μg |
| Adenine | 6.25 mg |
| Agar | 15 g |
| Distilled water | 1000 ml |

The fermentation beers were also assayed for activity at a dilution of 1:100 versus L1210 murine leukemia cells in vitro using the protocol detailed in Geran, Greenberg, MacDonald, Schumacher and Abbott, *Cancer Chemotherapy Reports*, Part 3, Vol. 3, No. 2 (1972). A fermentation beer which permitted 0–35% growth of the murine leukemia cells as compared to the growth of leukemia cells in a control tube was considered active. A fermentation beer which permitted no observable growth was considered most active. The antimicrobial and antitumor activity of the fermentation beers produced as described above appear in the data shown in Table VI. The crude fermentation beer was also found to exhibit antimicrobial activity against *Alcaligenes viscolactis, Bacillus subtilis, Escherichia coli,* and *Penicillium avellaneum.*

TABLE VI

Antimicrobial and Antitumor Activity (Versus L1210 Murine Leukemia Cells Grown In Vitro) of Fermentation Beers of Example 2

| | Antimicrobial Activity Versus *Streptococcus faecalis* Inhibition Zone Diameter (mm) (Using 12.7 mm Discs) | | Antitumor Activity Versus L1210 Murine Leukemia Cells |
|---|---|---|---|
| Sample | AM-9 Medium | AM-10 Medium | Percent Growth |
| 1 | 47 | 0 | 31 |
| 2 | 50 | 26 | 19 |

Stirred-Jar Fermentation

EXAMPLE 3

The ATCC 39364 culture, preserved cryogenically in vials, was thawed and used to inoculate a 2-liter baffled Erlenmeyer seed flask containing 600 ml of SD-05 seed medium. The inoculated flask contents were incubated at 33° C. for 72 hours.

The resulting microbial growth was used to inoculate 16 liters of SD-05 seed medium contained in a 30-liter stirred-jar fermentor. The stirred-jar contents were incubated at 33° C. for 24 hours while being stirred at 300 rpm and sparged with air at a rate of one volume/volume/minute. The resulting microbial growth was used to inoculate the four production stirred-jar fermentors.

Four 30-liter stirred jars, each containing 16 liters of SM-30 medium were sterilized by autoclaving for 40 minutes at 121° C. The jars and their contents were cooled at 33° C., and then each was inoculated with 800 ml of inoculum from the previously described batch. The four stirred-jar batches were subsequently incubated at 33° C. for three days while being stirred at 300 rpm and sparged with air at a rate of one volume/volume/minute.

The production of guanine-$N^7$-oxide in the fermentation beer was monitored throughout the fermentation cycle by measuring the growth inhibition zone diameter for *Streptococcus faecalis*, grown on AM-9 medium, according to the procedure described above. In addition, the percent sedimentation (percent growth) and pH of the fermentation beer were measured throughout the process. The data are presented in Table VII.

TABLE VII

Stirred-Jar Fermentative Production of Guanine-$N^7$-oxide

| Fermentation Time (Hours) | pH | Sedimentation Value (Percent Growth) | Antimicrobial Activity (Growth Inhibition Zone Diameter (mm) (Using 12.7 mm Discs) |
|---|---|---|---|
| Jar Number 1 | | | |
| 0 | 5.65 | | |
| 22 | 5.10 | 14.0 | 0 |
| 48 | 5.05 | 22.0 | 36 |
| 72 | 5.40 | 23.3 | 37 |
| 77 | 5.40 | 26.6 | 32 |
| Jar Number 2 | | | |
| 0 | 5.65 | | |
| 22 | 5.10 | 13.3 | 0 |
| 48 | 5.05 | 21.3 | 34 |
| 72 | 5.25 | 20.7 | 35 |
| 77 | 5.45 | 23.3 | 34 |
| Jar Number 3 | | | |
| 0 | 5.7 | | |
| 22 | 5.10 | 14.0 | 15 |
| 48 | 5.10 | 23.3 | 37 |
| 72 | 5.45 | 23.3 | 38 |
| 77 | 5.60 | 42.0 | 33 |
| Jar Number 4 | | | |
| 0 | 5.7 | | |
| 22 | 5.10 | 14.7 | 15 |
| 48 | 5.10 | 23.3 | 33 |
| 72 | 5.30 | 23.3 | 35 |
| 77 | 5.45 | 44.6 | 30 |

200-Gallon Fermentation Batch

EXAMPLE 4

A cryogenically preserved sample of isolate ATCC 39364 was thawed and a 1-ml sample was used to inoculate 600 ml of SD-05 medium contained in a 2-liter baffled Erlenmeyer flask. The flask contents were incubated for 72 hours at 33° C. while being shaken on a rotary gyratory shaker at 130 rpm (5 cm throw).

The resulting microbial growth was used to inoculate 16 liters of SD-05 seed medium in a 30-liter stirred-jar fermentor. The resulting inoculum was incubated for 24 hours at 33° C. while being stirred at 300 rpm and sparged with air at a rate of one volume/volume/minute.

A 200-gallon (757-liter) fermentator, containing 160 gallons (605.6 liters) of SM-30 medium was sterilized by autoclaving at 121° C. for 40 minutes. The medium was cooled to 33° C. and then inoculated with the 16-liter batch of inoculum prepared as described above. The inoculated medium was incubated at 33° C. for three days while being stirred at 155 rpm and sparged with air at one volume/volume/minute. Dow Corning "C" antifoaming agent was used to control foaming as needed.

The production of guanine-$N^7$-oxide was monitored throughout the fermentation cycle by assaying the antimicrobial activity of the beer against *Streptococcus faecalis* using the assay previously described. Fermentation parameters such as pH and sedimentation (percent growth) were also monitored, and the data appear in Table VIII.

TABLE VIII

Large-Batch Fermentative Production of Guanine-$N^7$-oxide

| Fermentation Time (Hours) | pH | Sedimentation Value (Percent Growth) | Antimicrobial Activity (Growth Inhibition Zone Diameter (mm) (Using 12.7 mm Discs) |
|---|---|---|---|
| 0 | 6.05 | | |
| 12 | 5.35 | 9.3 | |
| 24 | 5.30 | 13.3 | 0 |
| 36 | 5.00 | 20.0 | 22 |
| 48 | 5.20 | 21.3 | 32 |
| 54 | 5.10 | 20.0 | 34.5 |
| 60 | 5.20 | 20.0 | 37.5 |
| 72 | 5.45 | 23.3 | 38.0 |

Isolation of Guanine-$N^7$-oxide

EXAMPLE 5

Fifty pounds (23 kg) of Celite 545 were mixed with 99 gallons (374 liters) of whole beer from Example 4. The resulting mixture was filtered through an 18 inch (45.7 cm) plate-and-frame filter press and the filter cake washed with water to yield 125 gallons (473 liters) of filtrate.

A chromatographic column was filled with 14 liters of the chloride form of Dowex 1X2 resin (Dow Chemical Company, P.O. Box 1767, Midland, Mich. 48640). The resin was washed with 34 liters of deionized water and then charged with the filtered fermentation beer. The material adsorbed on the column was eluted with six 17-liter fractions of 0.5N acetic acid.

The six fractions were combined and concentrated to a volume of 20 liters. The pH of the solution was adjusted to 6.6 by addition of 500 ml of 50% aqueous sodium hydroxide solution. The resulting solution was further concentrated under vacuum to a volume of 2.4 liters.

A chromatographic column was filled with 17 kg of Sephadex G-10 (Pharmacia Fine Chemicals, 810 Centennial Ave., Piscataway, N.J. 08854). The 2.4-liter concentrate prepared above was charged to this column and eluted with a total volume of 58 liters of deionized water in 13 fractions ranging in volume from 2 liters to 18 liters. The fractions containing most of the antimicrobial activity (*Strept. faecalis,* AM-9 medium) were combined and concentrated in vacuo to a volume of 1.5 liters. Crude crystalline guanine-$N^7$-oxide precipitated from the combined eluate as it was concentrated, and the impure product was separated by decanting the supernate. The solid residue was washed with cold water, and dried to yield 2.2 g of crude guanine-$N^7$-oxide.

This material was dissolved in 60 ml of water, and the pH of the resulting solution was adjusted to pH 11 by the addition of aqueous sodium hydroxide solution. This solution was purified by passage through a Sephadex G-10 column. Nine fractions, varying in volume from 50 to 100 ml were collected and assayed by high pressure liquid chromatographic analysis and by antimicrobial assay. Those fractions shown by HPLC to contain guanine-$N^7$-oxide as the only ultraviolet absorbing substance were combined and lyophilized to yield 1.36 g of essentially pure guanine-$N^7$-oxide as its sodium salt.

To 60 ml of a solution containing approximately 450 mg of guanine-$N^7$-oxide sodium salt was added 1.0M acetic acid to pH 7.9. The white precipitate that formed was collected and dried to yield 276 mg partially crystalline neutral guanine-$N^7$-oxide. Additional 1.0M acetic acid was added to the mother liquor to a final pH of 5.9. After standing overnight at 5° C., an additional 46 mg of neutral guanine-$N^7$-oxide precipitated as a white crystalline solid.

The structure of the material isolated was unambiguously determined to be that of 2-amino-1,9-dihydro-6$\underline{H}$-purin-6-one-7-oxide by x-ray diffraction employing the heavy atom technique with the hydrobromide salt. The spectral properties of the material were also measured, and the data for the neutral form and the sodium salt appear in Table IX.

TABLE IX

Properties of Guanine-$N^7$-oxide and the Sodium Salt Derived by Fermentative Production from Actinomycete Isolate ATCC 39364

Elemental Analysis (Neutral guanine-$N^7$-oxide)

Calculated for $C_5H_5N_5O_2 \cdot 0.25\ H_2O$
  C = 34.99%   H = 3.21%   N = 40.81%   O = 20.99%
Found C = 34.97%   H = 3.41%   N = 40.76%   O = 20.55%
  35.17%   3.50%   41.00%   O = 20.58%

Ultraviolet Spectrum (Sodium salt)

Absorption maxima in aqueous solution
at pH 11: 291 nm (a = 23.6); 234 nm (a = 82.4)
at pH 1: 251 nm (a = 37.5); infection at 270 nm Infrared Spectrum (Sodium salt) in KBr Principal absorption peaks at 3360, 3200, 3120, 1680, 1640, 1540, 1520, 1450, 1325, and 1090 reciprocal centimeters.

Proton Magnetic Resonance Spectrum In $D_2O$ Containing NaOD (Sodium salt)

A single resonance line at 7.6 ppm downfield from tetramethylsilane.

$^{13}C$ Nuclear Magnetic Resonance Spectrum In $D_2O$ Containing NaOD (Sodium salt)

Signals at 109.72, 136.23, 155.34, 157.63, and 161.55 ppm downfield from tetramethylsilane.

High Pressure Liquid Chromatographic (HPLC) Data (Sodium salt)

Retention time of 3.97 minutes on a 3.9 mm i.d. × 30 cm μBondpack C-18 silica gel column (Waters Associates, Milford, MA); 0.05 M sodium phosphate buffer (pH 5.4); flow rate 1.5 ml/min.
Retention time of 2.32 minutes on a 3.9 mm i.d. × 30 cm μBondpack C-18 silica gel column (Waters Associates, Milford, MA); 0.05 M sodium phosphate buffer (pH 6.8); flow rate 1.0 ml/min.

Biological Activity of Guanine-$N^7$-oxide

EXAMPLE 6

The antimicrobial activity of pure guanine-$N^7$-oxide was evaluated by saturating 12.7 mm paper discs with an aqueous solution of guanine-$N^7$-oxide at a concentration of 1 mg/ml. The saturated paper discs were placed on a bioassay tray containing an agar medium seeded with a particular organism. The discs and inoculated medium were incubated for 16 hours at 37° C. and the diameter of the resulting zone of growth inhibition, if any, was measured. The data from these tests appear in Table X.

TABLE X

Antimicrobial Activity of Guanine-$N^7$-oxide

| Microorganism | Culture Number* | Medium | Diameter Inhibition Zone (mm) |
|---|---|---|---|
| Alcaligenes faecalis | ATCC 8750 | Mycin | 0 |
| Alcaligenes viscolactis | ATCC 21698 | T. soy | 0 |
| Bacillus subtilis | PD 04555 | #169 | 33.5 |
| Bacillus subtilis | PD 04969 | Br. thio. | 0 |
| Bacillus subtilis | PD 04969 | #169 | 36 |
| Bacillus subtilis | PD 04555 | Mycin | 0 |
| Branhamella catarrhalis | PD 03596 | CAP | 0 |
| Enterobacter aerogenes | PD 0126 | Mycin | 0 |
| Escherichia coli | ATCC 10536 | GAA | 0 |
| Escherichia coli | PD 05117 | #169 | 0 |
| Escherichia coli | PD 04524 | GAA | 0 |
| Escherichia coli | PD 04814 | #169 | 0 |
| Escherichia coli | PD 04863 | #169 | 28.5 |
| Escherichia coli | PD 04863 | GAA | 0 |
| Klebsiella pneumoniae | PD 05037 | CMA | 0 |
| Kloeckera africana | M1570 | #77 | 0 |
| Kloeckera brevis | M1378 | #69 | 0 |
| Micrococcus luteus | PD 05064 | PAS | 0 |
| Micrococcus lysodeikticus | PD 04783 | T. soy | 0 |
| Penicillium avellaneum | M2988 | H & B | 0 |
| Proteus vulgaris | 05062 | PAS | 0 |

TABLE X-continued

Antimicrobial Activity of Guanine-$N^7$—oxide

| Microorganism | Culture Number* | Medium | Diameter Inhibition Zone (mm) |
|---|---|---|---|
| *Pseudomonas aeruginosa* | NCTC 10490 | CMA | 0 |
| *Rhodotorula glutinis* | M1384 | #77 | 0 |
| *Saccharomyces cerevisiae* | 01525 | #77 | 0 |
| *Staphylococcus aureus* | PD 02482 | PAS | 0 |
| *Torulopsis albida* | M1390 | #102 | 0 |
| *Xanthomonas phaseoli* | PD 06002 | CMA | 0 |

*ATCC = American Type Culture Collection, Rockville, Maryland 20852.
PD or M = Parke-Davis/Warner-Lambert Culture Collection, 2800 Plymouth Road, Ann Arbor, Michigan 48105.
NCTC = National Culture Type Collection, London, England.

The in vivo antitumor activity of guanine-$N^7$-oxide was determined against P388 murine leukemia cells and L1210 murine leukemia cells employing the protocol described in *Cancer Chemotherapy Reports*, referenced above. The mice were infected intraperitoneally on Day 0 and then given the dose of guanine-$N^7$-oxide indicated in Table X on Days 1–5 in the case of the assay against P388 murine leukemia cells and on Days 1–9 in the case of the assay against L1210 murine leukemia cells. The results are presented in Table X in terms of % T/C values where:

$$\% \ T/C = \frac{\text{median survival time of treated mice}}{\text{median survival time of untreated mice}} \times 100$$

TABLE XI

In Vivo Antitumor Activity of Guanine-$N^7$—oxide Versus P388 Murine Leukemia and L1210 Murine Leukemia Cells

| Dosage (mg/kg Body Weight) | Activity Versus P388 Murine Leukemia Cells (% T/C) | | Activity Versus L1210 Murine Leukemia Cells (% T/C) | |
|---|---|---|---|---|
| | Test 1 | Test 2 | Test 1 | Test 2 |
| 50 | Toxic | Toxic | Toxic | Toxic |
| 25 | 142 | 126 | 134 | 164 |
| 12.5 | 145 | 130 | 168 | 234 |
| 6.25 | — | 130 | 168 | 172 |
| 3.12 | — | — | 138 | 144 |

EXAMPLE 8

Preparation of Guanine-N 7-oxide Hydrochloride

2-Amino-1,9-dihydro-6H-purin-6-one-7-oxide (52.3 mg, 0.31 mmol) was heated over a steam bath in 5 ml of 1.0M aqueous hydrochloric acid until it dissolved. The solution was filtered and allowed to cool to room temperature. Upon standing, 47.3 mg of the hydrochloride salt of 2-amino-1,9-dihydro-6H-purin-6-one-7-oxide precipitated as fine, white needles, mp >250° C.

Analysis: Calcd. for $C_5H_6N_5O_2$ Cl.0.9$H_2O$: C, 27.31%; H, 3.55%; N, 31.87%; Cl, 16.14%. Found: C, 27.22%; H, 3.48%; N, 31.53%; Cl, 16.73%.

EXAMPLE 9

Preparation of Guanine-N 7-oxide Hydrobromide

2-Amino-1,9-dihydro-6H-purin-6-one-7-oxide (50 mg, 0.29 mmol) was heated over a steam bath in 5 ml of 1.0M aqueous hydrobromic acid until it dissolved. The solution was filtered and cooled to room temperature for one hour and then allowed to stand at 5° C. overnight whereupon 33 mg of the hydrobromide salt of 2-amino-1,9-dihydro-6H-purin-6-one-7-oxide precipitated as white needles, mp >250° C.

The antibiotic compound guanine-$N^7$-oxide, either in its neutral form, or in the form of one or more of its pharmaceutically acceptable salts, is useful for this antimicrobial and antitumor activity as a pharmaceutical composition in combination with a compatible pharmaceutically acceptable carrier.

Guanine-$N^7$-oxide in one or more of its tautomeric forms is amphoteric, and is capable of forming salts with either acids or bases. The neutral form of guanine-$N^7$-oxide, in its various tautomeric isomeric modifications, as well as their salts with acids and bases are contemplated as falling within the scope of the present invention.

Appropriate pharmaceutically acceptable acid addition salts are derived from inorganic acids such as hydrochloric, hydrobromic, sulfuric, phosphoric and the like, and organic acids such as acetic, malonic, succinic, maleic, ethanesulfonic, benzenesulfonic, p-toluenesulfonic and the like.

The acid addition salts of the neutral form of guanine-$N^7$-oxide are prepared either by dissolving the compound in water or aqueous alcohol or in other suitable solvents containing the appropriate acid and isolating the salt by evaporating the solvent, or by reacting the guanine-$N^7$-oxide and acid in an organic solvent, in which case the salt separates directly or can be obtained by concentration of the solution.

Alternatively, guanine-$N^7$-oxide in its various acidic tautomeric forms may be converted to a metal, ammonium, or organic amine salt, for example, by suspending the compound in a suitable solvent such as water, aqueous alcohol or other suitable solvent, and adjusting the pH with a pharmaceutically acceptable metal base, ammonium hydroxide, or organic amine base, and then subsequently removing the solvent under reduced pressure. The neutral form may be regenerated, if desired, by treating the salt form with an acid. For example, dilute aqueous acetic acid may be utilized to regenerate the neutral form of the compound from a particular salt. While the neutral form and the various salts vary somewhat from one another in their physical properties such as solubility in polar solvents, the neutral form and the various salts are considered equivalent for purposes of this invention.

By the term alkyl group is meant, throughout this specification and the appended claims, branched and unbranched saturated hydrocarbon groupings.

The term "pharmaceutically acceptable metal" cation contemplates the positively charged ions derived from such metals as sodium, potassium, magnesium, calcium, aluminum, zinc, iron, and the like.

The term "pharmaceutically acceptable amine" cation contemplates the positively charged ammonium ion and analogous ions derived from organic nitrogenous bases strong enough as bases to form salts with guanine-$N^7$-oxide.

Bases useful for the purpose of forming pharmaceutically acceptable nontoxic addition salts of guanine-$N^7$-oxide form a class whose limits are readily understood to those skilled in the art. For purposes of illustration, the class can be said to comprise amine cations of the formula:

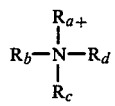

wherein Ra, Rb, Rc, and Rd, independently may be hydrogen or alkyl of from one to six carbon atoms, cycloalkyl of from about three to about six carbon atoms, aryl, alkylaryl of from about seven to about ten carbon atoms, hydroxyalkyl of from two to four carbon atoms, or monoarylhydroxyalkyl of from about 8 to about 15 carbon atoms. Further, when taken together with the nitrogen atom to which they are attached, any two of Ra, Rb, and Rc may form part of a 5-membered or 6-membered nitrogen heterocyclic aromatic or non-aromatic ring containing carbon or oxygen, said nitrogen heterocyclic rings being unsubstituted, monosubstituted or disubstituted with alkyl groups of from one to six carbon atoms.

Specific examples of organic amine cations contemplated as falling within the scope of the present invention include mono-, di-, tri-, and tetramethylammonium, mono-, di-, and triethylammonium, mono-, di-, and tripropylammonium (n-propyl and iso-propyl), ethyldimethylammonium, benzylammonium, dibenzylammonium, benzyldimethylammonium, cyclohexylammonium, piperidinium, morpholinium, pyrrolidinium, 4-ethylmorpholinium, 1-isopropylpyrrolidinium, 1,4-dimethylpiperazinium, 1-n-butylpiperdininum, 2-methylpiperidinium, 1-ethyl-2-methylpiperidinium, mono-, di-, and triethanolammonium, ethyldiethanolammonium, n-butylmonoethanolammonium, tris(hydroxymethyl)-methylammonium, phenylmonoethanolammonium, and the like.

Pharmaceutical compositions falling within the scope of this invention may also contain other antimicrobial and/or antitumor agents. The compositions may be made up in any pharmaceutically appropriate form for the desired route of administration. Examples of such forms include solid forms for oral administration as tablets, capsules, pills, powders and granules, liquid forms for topical or oral administration as solutions, suspensions, syrups, and elixirs, and forms suitable for parenteral administration such as sterile solutions, suspensions, or emulsions.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.1 mg to 500 mg preferably to 5 to 100 mg according to the particular application and the potency of the active ingredient. The compositions can, if desired, also contain other compatible therapeutic agents.

In therapeutic use, the mammalian dosage range for a 70 kg subject is from 1 to 1500 mg/kg of body weight per day or preferably 2 to 750 mg/kg of body weight per day. The dosages, however, may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

We claim:

1. The compound 2-amino-1,9-dihydro-6$\underline{H}$-purin-6-one-7-oxide and its tautomers and the pharmaceutically acceptable salts thereof.

2. The compound in accordance with claim 1 having the name 2-amino-1,9-dihydro-6$\underline{H}$-purin-6-one-7-oxide hydrochloride.

3. The compound in accordance with claim 1 having the name 2-amino-1,9-dihydro-6$\underline{H}$-purin-6-one-7-oxide hydrobromide.

4. The compound in accordance with claim 1 having the name 2-amino-1,9-dihydro-6$\underline{H}$-purin-6-one-7-oxide sodium salt.

5. A pharmaceutical composition for treating microbial infections in a mammal comprising an antimicrobially effective amount of a compound defined by claim 1 together with a pharmaceutically acceptable carrier.

* * * * *